United States Patent [19]

Wullbrandt et al.

[11] Patent Number: 4,767,880

[45] Date of Patent: Aug. 30, 1988

[54] PROCESS FOR RACEMIZING OPTICALLY ACTIVE ALPHA-PHENOXYPROPIONIC ACID AND DERIVATIVES THEREOF

[75] Inventors: Dieter Wullbrandt, Hofheim am Taunus; Merten Schlingmann, Königstein, both of Fed. Rep. of Germany

[73] Assignee: Hoechst Aktiengesellschaft, Fed. Rep. of Germany

[21] Appl. No.: 66,570

[22] Filed: Jun. 26, 1987

[30] Foreign Application Priority Data

Jun. 28, 1986 [DE] Fed. Rep. of Germany ....... 3621835

[51] Int. Cl.$^4$ .............................................. C07C 69/76
[52] U.S. Cl. .................................... 560/061; 562/401
[58] Field of Search .......................... 560/61; 562/401

[56] References Cited

U.S. PATENT DOCUMENTS 3,717,669 2/1973 Grant ................................... 560/061
3,759,950 9/1973 Grant ................................... 560/061

FOREIGN PATENT DOCUMENTS 61-83144 4/1986 Japan ................................ 59/125 A Primary Examiner—Paul J. Killos
Attorney, Agent, or Firm—Finnegan, Henderson Farabow, Garrett and Dunner

[57] ABSTRACT

Optically active enantiomers of alkyl α-phenoxypropionates, and of derivatives thereof, can be racemized in good yields and without formation of decomposition products with the aid of an alkali metal ($C_1$–$C_5$) alcoholate, an alkali metal hydroquinone, an alkali metal phenolate or an alkali metal hydroxyphenoxypropionate, or derivatives thereof.

8 Claims, No Drawings

PROCESS FOR RACEMIZING OPTICALLY ACTIVE ALPHA-PHENOXYPROPIONIC ACID AND DERIVATIVES THEREOF

Many synthetic phytohormones and herbicides, known from the literature, or the precursors thereof, such as, for example, α-phenoxypropionic acid, exist in the form of racemates on use or further processing. However, one of the optically active isomers is frequently more active than the other or than the racemate. Since it is often more economic to employ the relevant substance only in the more active form, attempts are being made to resolve the racemates into their enantiomers. However, in order not to have to be satisfied with a 50% yield, attempts are made in many cases to racemize the inactive isomer and to return into the cycle the racemates resulting therefrom. In this fashion, a continuous process for the preparation of the desired optically active compound is achieved.

In a publication (Biotechnol., Bioeng., Vol 26, 1449, 1984) Cambou and Klibanov describe complete racemization of methyl L-chlorophenoxypropionate by incubating the substance, dissolved in methanol, at 60° C. over a period of 16 hours in the presence of catalytic amounts of sodium methanolate. In other processes, racemization is achieved by heating in the presence of a catalyst or solvent, such as, for example, 2-aminoalkyl or aryl compounds (German Offenlegungsschrift No. 2,903,589 and Japanese Preliminary Published Application 50/050,317), or by heating N-acylamino acids with carboxylic acids (German Offenlegungsschrift No. 3,334,849A1).

However, it has been found that derivatives of α-phenoxypropionic acid are decomposed by heating to about 250° in the solid phase or by adding hydroquinone.

Surprisingly, it has now been found that the two stereoisomeric forms of α-phenoxypropionic acid, and of the derivatives thereof, can be racemized in good yields, without formation of decomposition products, with the aid of alkali metal alcoholates in the broad sense and an alkali metal hydroxyphenoxypropionate.

The invention thus relates to a process for racemization of optically active enantiomers, wherein the compound of the general formula I,

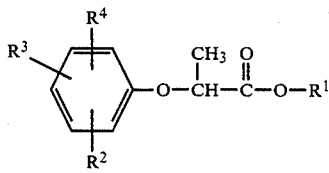

in which (a) $R^1$ denotes an alkyl group, having up to 8 carbon atoms, which can in each case be substituted by hydroxyl, halogen, alkyl and/or nitro, or a cyclic alkyl group having up to 6 carbon atoms and (b) $R^2$ denotes hydrogen, hydroxyl or an alkoxy group or an aryloxy group or an oxygen-bound, heterocyclic ring system, in each case having up to 10 carbon atoms, and (c) $R^3$ and $R^4$, independently of one another, denote hydrogen or halogen, is racemized with the aid of an alkali metal ($C_1$–$C_5$) alcoholate, an alkali metal hydroquinone, an alkali metal phenolate and/or an alkali metal hydroxyphenoxypropionate or derivatives thereof which carry substituents on the aromatic ring.

following

The invention is described below in detail and defined in the claims.

The starting materials are the alkyl esters of α-phenoxypropionic acid and of the abovementioned derivatives thereof. As a chain, the alkyl ester groups $R^1$ can contain up to 8 carbon atoms, which may be substituted, or, as a cyclic alkyl group, they can contain up to 6 carbon atoms. Lower linear alkyl groups having up to 5 carbon atoms, in particular unbranched alkyl groups having 1 to 3 carbon atoms are preferred.

In the following reaction procedure according to the invention, the optically active ester is employed dissolved in a solvent. Suitable for this are, for example, inert organic solvents in which the L- and D-esters are soluble. Hydrocarbons, such as alkanes having a chain length up to 10 carbon atoms, and toluene or xylene, dialkyl ethers having a chain length up to 6 carbon atoms such as, for example, di-isopropyl ether, methyl isobutyl ether, methyl isopropyl ether and tert.butyl methyl ether, and dialkyl ketones having a chain length up to 6 carbon atoms, such as, for example, methyl ethyl ketone and methyl isobutyl ketone, are preferably used.

Alcohols are furthermore preferred, the alcohol which corresponds to the chain length of the alkyl group $R^1$ of general formula I being employed in particular. As mentioned above, racemization is carried out by adding an alkali metal ($C_1$–$C_5$) alcoholate, preferably an alkali metal ($C_2$–$C_4$) alcoholate, an alkali metal hydroquinone, an alkali metal phenolate or an alkali metal hydroxyphenoxypropionate. Derivatives of the aromatic compounds mentioned can also be used, in particular those which carry, on the aromatic ring, up to two additional substituents which, independently of one another, are hydrogen, halogen, alkyl and alkoxy.

The reagents are employed in concentrations of 1 to 10 mole percent, preferably 3 to 8 mole percent. If α-phenoxypropionic esters, or derivatives thereof with alkali metal ($C_1$–$C_5$) alcoholates, are racemized, more than 1.0 mole of base per mole of ester must be employed. Using the other reagents mentioned, catalytic amounts are required. The reaction mixture is heated to 100 to 200° C. and incubated for 30 minutes to 8 hours, preferably 2 to 4 hours.

If the racemization is carried out using alkali metal ($C_1C_5$) alcoholate, the acid is obtained essentially quantitatively as the final product in an alkaline medium, or as the ester in an acidic medium.

The final products are separated off from the reaction mixture by methods which are known per se, by acidification and extraction with a relatively nonpolar solvent, such as, for example, diethyl ether, in the case of the acid, or, for example, by distillation in the case of the ester.

The invention is described in greater detail with reference to examples. Percentage data refer to the weight, unless otherwise stated.

EXAMPLE 1

10 g of ethyl L-2-(4-hydroxyphenoxy)propionate were maintained under reflux for 2 hours in a solution of 50 ml of tert.butyl methyl ether and 22 ml of 30% strength sodium methylate solution. After cooling, 50 ml of water were added to the reaction mixture, the aqueous phase was separated off, and a pH of 2.0 was produced using hydrochloric acid. The D,L-acid was extracted with 50 ml of diethyl ether. After drying using sodium sulfate, the organic phase was concentrated to 10 ml, and 10–20 ml of n-hexane were added to the racemic acid for crystallization. Yield: 6.8 g of D,L-2-(4-hydroxyphenoxy)propionic acid.

EXAMPLE 2

10 g of ethyl L-2-(4-hydroxyphenoxy)propionate were heated at the boiling point for 2 hours in a solution of 50 ml of tert.butyl methyl ether and 12 ml of 30% strength sodium ethylate solution. After cooling, 5 ml of glacial acetic acid and subsequently 20 ml of water were added to the reaction mixture. The organic phase was separated off and dried, and the solvent was removed in vacuo. Yield: 7.9 g of ethyl D,L-2-(4-hydroxyphenoxy)-propionate.

EXAMPLE 3

100 mg of hydroquinone were converted into the monopotassium salt by adding 9 ml of 0.1 molar ethanolic potassium hydroxide solution. The ethanol was removed in vacuo, and 3 g of ethyl L-2-(4-hydroxyphenoxy)propionate ($[\alpha]_a^{20}$ 41° (c=2, in chloroform)) were added to the residue. The mixture was subsequently stirred for 3 hours at 170° C. with exclusion of air. After cooling the reaction mixture, the racemic ethyl hydroxyphenoxypropionate was separated off by distillation at 130° C. and 0.1 torr. Yield: 2.4 g (80% of theory) of ethyl D,L-2-(4- hydroxyphenoxy)propionate.

EXAMPLE 4

An analogous procedure to Example 3 was carried out, with addition of 100 mg of sodium phenolate. After working up, 2.5 g of racemic ethyl D,L-2-(4-hydroxyphenoxy)propionate were obtained.

EXAMPLE 5

0.3 g of 2-(4-hydroxyphenoxy)propionic acid in the form of the sodium salt was added to 3 g of ethyl L-2-(4-hydroxyphenoxy)propionate. The reaction mixture was warmed to 160, 180 and 200° C. with exclusion of air. After working up according to Example 3, the racemization was determined with the aid of the specific rotation in chloroform.

| Time [h] | Temperature [°C.] | Specific rotation $[\alpha]_D^{20}$ |
| --- | --- | --- |
| 3 | 160 | −33.0° |
| 3 | 180 | −24.2° |
| 3 | 200 | −3.2° |
| 1 | 200 | −9.7° |

We claim:

1. A process for racemization of optically active enantiomers, wherein the compound of the formula I,

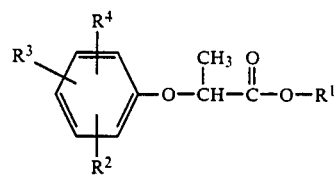

in which
(a) $R^1$ denotes an alkyl group, having up to 8 carbon atoms, which can in each case be substituted by hydroxyl, halogen, alkyl and/or nitro, or a cyclic alkyl group having up to 6 carbon atoms and
(b) $R^2$ denotes hydrogen, hydroxyl, or an alkoxy group or an aryloxy group or an oxygen-bound, heterocyclic ring system, in each case having up to 10 carbon atoms, and
(c) $R^3$ and $R^4$, independently of one another, denote hydrogen or halogen, is racemized with the aid of an alkali metal ($C_1$–$C_5$) alcoholate, an alkali metal hydroquinone, an alkali metal phenolate and/or an alkali metal hydroxyphenoxypropionate or derivatives thereof which carry substituents on the aromatic ring.

2. The process as claimed in claim 1, wherein an alkali metal hydroquinone, an alkali metal phenolate and/or an alkali metal hydroxyphenoxypropionate is employed which in each case carries, on the aromatic ring, up to two additional substituents which, independently of one another, are oxygen, halogen, alkyl or alkoxy.

3. The process as claimed in claim 1, wherein the reaction is carried out in an inert organic solvent.

4. The process as claimed in claim 3, wherein the solvent employed is an alkane having a chain length up to 10 carbon atoms, or toluene or xylene or a dialkyl ether having a chain length up to 6 carbon atoms or a dialkyl ketone having chain length up to 6 carbon atoms, or the alcohol which corresponds in chain length to the alkyl group $R^1$ of the esters of the formula I.

5. The process as claimed in claim 1, wherein the racemization is carried out at 100 to 200° C. over a period of 30 minutes to 8 hours.

6. The process as claimed in claim 5, wherein the racemization proceeds over a period of 2 to 4 hours.

7. The process as claimed in claim 1 wherein the reagents are employed in a concentration of 1 to 10 mole percent.

8. The process as claimed in claim 7, wherein the reagents are employed in a concentration of 3–8 mole percent.

* * * * *